ized eyewear.

(12) United States Patent
Mason et al.

(10) Patent No.: US 10,722,128 B2
(45) Date of Patent: Jul. 28, 2020

(54) HEART RATE DETECTION SYSTEM AND METHOD

(71) Applicant: Vision Service Plan, Rancho Cordova, CA (US)

(72) Inventors: Walter M. Mason, Sacramento, CA (US); Richard Chester Klosinski, Jr., Sacramento, CA (US); Matthew Allen Workman, Sacramento, CA (US); Shaun Patrick Garland, Sacramento, CA (US); Jason Lomnitz, Sacramento, CA (US); Jay William Sales, Sacramento, CA (US)

(73) Assignee: Vision Service Plan, Rancho Cordova, CA (US)

( * ) Notice: Subject to any disclaimer, the term of this patent is extended or adjusted under 35 U.S.C. 154(b) by 0 days.

(21) Appl. No.: 16/527,544

(22) Filed: Jul. 31, 2019

(65) Prior Publication Data
US 2020/0037946 A1 Feb. 6, 2020

Related U.S. Application Data

(60) Provisional application No. 62/713,493, filed on Aug. 1, 2018.

(51) Int. Cl.
*A61B 5/024* (2006.01)
*A61B 5/00* (2006.01)
(Continued)

(52) U.S. Cl.
CPC ........ *A61B 5/02427* (2013.01); *A61B 5/0077* (2013.01); *A61B 5/222* (2013.01);
(Continued)

(58) Field of Classification Search
CPC .......... A61B 5/02427–02433; A61B 5/02444; A61B 5/6803; A61B 5/6821;
(Continued)

(56) References Cited

U.S. PATENT DOCUMENTS

| 3,505,879 A | 4/1970 | Vanderberg |
| 3,548,663 A | 12/1970 | Radin |

(Continued)

FOREIGN PATENT DOCUMENTS

| EP | 2778612 | 12/2017 |
| GB | 2396421 | 6/2004 |

(Continued)

OTHER PUBLICATIONS

Final Office Action, dated Apr. 29, 2019, from corresponding U.S. Appl. No. 15/791,196.
(Continued)

*Primary Examiner* — Angela M Hoffa
(74) *Attorney, Agent, or Firm* — Brient IP Law, LLC

(57) ABSTRACT

Computerized eyewear and corresponding methods measure a wearer's heart rate using a first optical sensor and a second optical sensor at least partially embedded in an eyewear temple. The first optical sensor transmits a first signal to a temple of the wearer and the second optical sensor transmits a second signal to the temple of the wearer. Reflections of the first signal are used to measure a raw heart rate delta and reflections of the second signal are used to measure a noise delta. The raw heart rate delta and the noise delta are used to determine a measured heart rate of the wearer of the computerized eyewear.

18 Claims, 5 Drawing Sheets

(51) Int. Cl.
*A61B 5/22* (2006.01)
*G02C 11/00* (2006.01)
A61B 5/0205 (2006.01)
G02C 5/14 (2006.01)
G02C 5/00 (2006.01)

(52) U.S. Cl.
CPC ............ *A61B 5/6803* (2013.01); *G02C 11/10* (2013.01); *A61B 5/0205* (2013.01); *A61B 5/6821* (2013.01); *G02C 5/001* (2013.01); *G02C 5/14* (2013.01)

(58) Field of Classification Search
CPC ..... A61B 5/6814; A61B 5/6815; G02C 11/10; G02C 5/001; G02C 5/14
See application file for complete search history.

(56) References Cited

U.S. PATENT DOCUMENTS

| | | | |
|---|---|---|---|
| 3,972,038 A | 7/1976 | Fletcher et al. |
| 4,100,401 A | 7/1978 | Tutt et al. |
| 4,186,609 A | 2/1980 | Baermann |
| 4,195,642 A | 4/1980 | Price et al. |
| 4,281,663 A | 8/1981 | Pringle |
| 4,407,295 A | 10/1983 | Steuer et al. |
| 4,434,801 A | 3/1984 | Jiminez et al. |
| 4,855,942 A | 8/1989 | Bianco |
| 4,878,749 A | 11/1989 | McGee |
| 4,919,530 A | 4/1990 | Hyman |
| 5,422,816 A | 6/1995 | Sprague et al. |
| 5,452,480 A | 9/1995 | Ryden |
| 5,497,143 A | 3/1996 | Matsuo et al. |
| 5,585,871 A | 12/1996 | Linden |
| 5,670,872 A | 9/1997 | Van De Walle et al. |
| 5,746,501 A | 5/1998 | Chien et al. |
| 5,891,042 A | 4/1999 | Sham et al. |
| 5,931,764 A | 8/1999 | Freeman et al. |
| 5,966,680 A | 10/1999 | Butnaru |
| 5,976,083 A | 11/1999 | Richardson et al. |
| 6,013,007 A | 1/2000 | Root et al. |
| 6,183,425 B1 | 2/2001 | Whalen et al. |
| 6,218,958 B1 | 4/2001 | Eichstaedt et al. |
| 6,241,684 B1 | 6/2001 | Amano et al. |
| 6,325,507 B1 | 12/2001 | Jannard et al. |
| 6,381,482 B1 | 4/2002 | Jayaraman et al. |
| 6,431,705 B1 | 8/2002 | Linden |
| 6,439,067 B1 | 8/2002 | Goldman et al. |
| 6,513,532 B2 | 2/2003 | Mault et al. |
| 6,532,298 B1 | 3/2003 | Cambier et al. |
| 6,736,759 B1 | 5/2004 | Stubbs et al. |
| 6,769,767 B2 | 8/2004 | Swab et al. |
| 6,783,501 B2 | 8/2004 | Takahashi et al. |
| 6,790,178 B1 | 9/2004 | Mault et al. |
| 6,812,845 B2 | 11/2004 | Yuzuki et al. |
| 7,181,345 B2 | 2/2007 | Rosenfeld et al. |
| 7,187,960 B2 | 3/2007 | Abreu |
| 7,192,136 B2 | 3/2007 | Howell et al. |
| 7,255,437 B2 | 8/2007 | Howell et al. |
| 7,376,238 B1 | 5/2008 | Rivas et al. |
| 7,380,936 B2 | 6/2008 | Howell et al. |
| 7,400,257 B2 | 7/2008 | Rivas |
| 7,401,918 B2 | 7/2008 | Howell et al. |
| 7,438,410 B1 | 10/2008 | Howell et al. |
| 7,454,002 B1 | 11/2008 | Gardner et al. |
| 7,457,434 B2 | 11/2008 | Azar |
| 7,481,531 B2 | 1/2009 | Howell et al. |
| 7,488,294 B2 | 2/2009 | Torch |
| 7,500,746 B1 | 3/2009 | Howell et al. |
| 7,500,747 B2 | 3/2009 | Howell et al. |
| 7,515,054 B2 | 4/2009 | Torch |
| 7,543,934 B2 | 6/2009 | Howell et al. |
| 7,581,833 B2 | 9/2009 | Howell et al. |
| 7,621,634 B2 | 11/2009 | Howell et al. |
| 7,630,524 B2 | 12/2009 | Lauper et al. |
| 7,634,379 B2 | 12/2009 | Noble |
| 7,640,135 B2 | 12/2009 | Vock et al. |
| 7,648,463 B1 | 1/2010 | Elhag et al. |
| 7,677,723 B2 * | 3/2010 | Howell .................. G02C 11/10 351/158 |
| 7,771,046 B2 | 8/2010 | Howell et al. |
| 7,792,552 B2 | 9/2010 | Thomas et al. |
| 7,793,361 B2 | 9/2010 | Ishihara et al. |
| 7,857,772 B2 | 9/2010 | Bouvier et al. |
| 7,806,525 B2 | 10/2010 | Howell et al. |
| 7,922,321 B2 | 4/2011 | Howell et al. |
| 7,987,070 B2 | 7/2011 | Kahn et al. |
| 8,007,450 B2 | 8/2011 | Williams |
| 8,011,242 B2 | 9/2011 | O'Neill et al. |
| 8,081,082 B2 | 12/2011 | Malik et al. |
| 8,109,629 B2 | 2/2012 | Howell et al. |
| 8,157,730 B2 | 4/2012 | Leboeuf et al. |
| 8,188,868 B2 | 5/2012 | Case |
| 8,202,148 B2 | 6/2012 | Young |
| 8,290,558 B1 * | 10/2012 | Lash .................. A61B 5/6843 600/323 |
| 8,294,581 B2 | 10/2012 | Kamen |
| 8,303,311 B2 | 11/2012 | Forest |
| 8,337,013 B2 | 12/2012 | Howell et al. |
| 8,384,617 B2 | 2/2013 | Braun et al. |
| 8,430,507 B2 | 4/2013 | Howell et al. |
| 8,448,846 B2 | 5/2013 | Needhan et al. |
| 8,449,471 B2 | 5/2013 | Tran |
| 8,465,151 B2 | 6/2013 | Howell et al. |
| 8,494,507 B1 | 7/2013 | Tedesco et al. |
| 8,500,271 B2 | 8/2013 | Howell et al. |
| 8,510,166 B2 | 8/2013 | Neven |
| 8,531,355 B2 | 9/2013 | Maltz |
| 8,540,583 B2 | 9/2013 | Leech |
| 8,568,313 B2 | 10/2013 | Sadhu |
| 8,594,971 B2 | 11/2013 | Keal et al. |
| 8,620,600 B2 | 12/2013 | Vock et al. |
| 8,630,633 B1 | 1/2014 | Tedesco et al. |
| 8,634,701 B2 | 1/2014 | Kang et al. |
| 8,647,270 B2 | 2/2014 | Leboeuf et al. |
| 8,690,750 B2 | 4/2014 | Krueger |
| 8,696,113 B2 | 4/2014 | Lewis |
| 8,733,928 B1 | 5/2014 | Lewis |
| 8,750,971 B2 | 6/2014 | Tran |
| 8,764,651 B2 | 7/2014 | Tran |
| 8,849,610 B2 | 9/2014 | Molettiere et al. |
| 8,892,401 B2 | 11/2014 | Yuen et al. |
| 8,905,542 B2 | 12/2014 | Howell et al. |
| 8,911,087 B2 | 12/2014 | Publicover et al. |
| 8,920,332 B2 | 12/2014 | Hong et al. |
| 8,931,896 B2 | 1/2015 | Blum et al. |
| 8,941,560 B2 | 1/2015 | Wong et al. |
| 8,944,590 B2 | 2/2015 | Blum et al. |
| 8,961,415 B2 | 2/2015 | Leboeuf et al. |
| 8,964,298 B2 | 2/2015 | Haddick et al. |
| 8,965,730 B2 | 2/2015 | Yuen |
| 8,979,295 B2 | 3/2015 | Waters |
| 9,001,427 B2 | 4/2015 | Jacobs et al. |
| 9,005,129 B2 | 4/2015 | Venkatraman et al. |
| 9,007,220 B2 | 4/2015 | Johns et al. |
| 9,028,405 B2 | 5/2015 | Tran |
| 9,031,812 B2 | 5/2015 | Roberts et al. |
| 9,033,493 B2 | 5/2015 | Howell et al. |
| 9,035,970 B2 | 5/2015 | Lamb et al. |
| 9,050,033 B2 | 6/2015 | Yoneyama et al. |
| 9,064,342 B2 | 6/2015 | Yuen et al. |
| 9,112,701 B2 | 8/2015 | Sano et al. |
| 9,113,794 B2 | 8/2015 | Hong et al. |
| 9,113,795 B2 | 8/2015 | Hong et al. |
| 9,141,194 B1 | 9/2015 | Keyes et al. |
| 9,144,405 B2 | 9/2015 | Kim et al. |
| 9,149,212 B2 | 10/2015 | Mori |
| 9,153,074 B2 | 10/2015 | Zhou et al. |
| 9,215,290 B2 | 12/2015 | Yuen et al. |
| 9,229,227 B2 | 1/2016 | Border et al. |
| 9,235,064 B2 | 1/2016 | Lewis |
| 9,239,473 B2 | 1/2016 | Lewis |
| 9,241,635 B2 | 1/2016 | Yuen et al. |
| 9,244,293 B2 | 1/2016 | Lewis |

(56) References Cited

U.S. PATENT DOCUMENTS

| | | |
|---|---|---|
| 9,247,212 B2 | 1/2016 | Bose et al. |
| 9,254,100 B2 | 2/2016 | Beck et al. |
| 9,256,711 B2 | 2/2016 | Horseman |
| 9,267,800 B2 | 2/2016 | Doutaz et al. |
| 9,304,331 B2* | 4/2016 | Carrara .................. G02C 3/003 |
| 9,341,526 B2 | 5/2016 | Bass et al. |
| 9,342,610 B2 | 5/2016 | Liu et al. |
| 9,480,877 B2 | 11/2016 | Chiang et al. |
| 9,520,638 B2 | 12/2016 | Baringer et al. |
| 9,529,197 B2 | 12/2016 | Olsson et al. |
| 9,566,033 B2 | 2/2017 | Bogdanovich et al. |
| 9,579,060 B1 | 2/2017 | Lisy et al. |
| 9,610,476 B1 | 4/2017 | Tran et al. |
| 9,726,904 B1 | 8/2017 | Lin |
| 9,763,592 B2 | 9/2017 | Le et al. |
| 9,782,128 B2* | 10/2017 | Lee ...................... A61B 5/0008 |
| 9,896,154 B2 | 2/2018 | Modolo |
| 9,977,259 B2 | 5/2018 | Archambeau et al. |
| 10,092,244 B2* | 10/2018 | Chuang ............. A61B 5/02427 |
| 10,188,323 B2 | 1/2019 | Sales et al. |
| 10,310,296 B2 | 6/2019 | Howell et al. |
| 10,330,956 B2 | 6/2019 | Howell et al. |
| 10,349,887 B1* | 7/2019 | Tzvieli ............... A61B 5/02125 |
| 10,398,328 B2* | 9/2019 | Kirenko ............... A61B 5/0002 |
| 2001/0031031 A1 | 10/2001 | Ogawa et al. |
| 2002/0151810 A1 | 10/2002 | Wong et al. |
| 2003/0195398 A1 | 10/2003 | Suzuki et al. |
| 2004/0039517 A1 | 2/2004 | Biesinger et al. |
| 2005/0033200 A1 | 2/2005 | Soehren et al. |
| 2005/0036103 A1 | 2/2005 | Bloch |
| 2005/0054942 A1 | 3/2005 | Melker et al. |
| 2006/0115130 A1 | 6/2006 | Kozlay |
| 2007/0052672 A1 | 3/2007 | Ritter et al. |
| 2007/0112287 A1 | 5/2007 | Fancourt et al. |
| 2007/0273611 A1 | 11/2007 | Torch |
| 2008/0137916 A1 | 6/2008 | Lauber et al. |
| 2009/0030350 A1 | 1/2009 | Yang et al. |
| 2009/0195747 A1 | 8/2009 | Insua |
| 2009/0227853 A1 | 9/2009 | Wijesiriwardana |
| 2009/0267805 A1 | 10/2009 | Jin et al. |
| 2010/0042430 A1 | 2/2010 | Bartfeld |
| 2010/0045928 A1 | 2/2010 | Levy |
| 2010/0110368 A1 | 5/2010 | Chaum |
| 2010/0136508 A1 | 6/2010 | Zekhtser |
| 2010/0271587 A1 | 10/2010 | Pavlopoulos |
| 2010/0280336 A1 | 11/2010 | Giftakis et al. |
| 2010/0308999 A1 | 12/2010 | Chornenky |
| 2010/0332571 A1 | 12/2010 | Healey et al. |
| 2011/0054359 A1 | 3/2011 | Sazonov et al. |
| 2011/0169932 A1 | 7/2011 | Mula et al. |
| 2011/0221656 A1 | 9/2011 | Haddick et al. |
| 2011/0224505 A1 | 9/2011 | Sadhu |
| 2012/0021806 A1 | 1/2012 | Maltz |
| 2012/0029367 A1 | 2/2012 | Hobeika |
| 2012/0127423 A1 | 5/2012 | Blum et al. |
| 2012/0133885 A1 | 5/2012 | Howell et al. |
| 2012/0135384 A1 | 5/2012 | Nakao |
| 2012/0142443 A1 | 6/2012 | Savarese et al. |
| 2012/0150047 A1* | 6/2012 | Terumoto ........... A61B 5/02427 |
| | | 600/479 |
| 2012/0169990 A1 | 7/2012 | Burnstein |
| 2012/0191016 A1 | 7/2012 | Jastram |
| 2012/0203310 A1 | 8/2012 | Pugh et al. |
| 2012/0206485 A1 | 8/2012 | Osterhout et al. |
| 2012/0310442 A1 | 12/2012 | Doutaz et al. |
| 2013/0009907 A1 | 1/2013 | Rosenberg et al. |
| 2013/0024022 A1 | 1/2013 | Bowers |
| 2013/0024211 A1 | 1/2013 | Monteforte et al. |
| 2013/0041590 A1 | 2/2013 | Burich et al. |
| 2013/0050258 A1 | 2/2013 | Liu et al. |
| 2013/0096397 A1 | 4/2013 | Kiso et al. |
| 2013/0138413 A1 | 5/2013 | Finch et al. |
| 2013/0157232 A1 | 6/2013 | Efirenkranz Joel |
| 2013/0242262 A1 | 9/2013 | Lewis |
| 2013/0274587 A1 | 10/2013 | Coza et al. |
| 2013/0274904 A1 | 10/2013 | Coza et al. |
| 2013/0307670 A1 | 11/2013 | Ramaci |
| 2013/0329183 A1 | 12/2013 | Blum et al. |
| 2013/0345168 A1 | 12/2013 | Kim et al. |
| 2014/0028456 A1 | 1/2014 | Sadhu |
| 2014/0031703 A1 | 1/2014 | Rayner et al. |
| 2014/0063242 A1 | 3/2014 | Hanina et al. |
| 2014/0073081 A1 | 3/2014 | Wang |
| 2014/0078049 A1 | 3/2014 | Parshionikar |
| 2014/0085190 A1 | 3/2014 | Erinjippurath et al. |
| 2014/0135593 A1 | 5/2014 | Jayalth et al. |
| 2014/0142459 A1 | 5/2014 | Jayalth et al. |
| 2014/0159862 A1 | 6/2014 | Yang et al. |
| 2014/0204334 A1 | 7/2014 | Stoll |
| 2014/0207264 A1 | 7/2014 | Quy |
| 2014/0218281 A1 | 8/2014 | Amayen et al. |
| 2014/0228649 A1 | 8/2014 | Rayner et al. |
| 2014/0229220 A1 | 8/2014 | Yuen et al. |
| 2014/0247145 A1 | 9/2014 | Proud |
| 2014/0266988 A1 | 9/2014 | Fisher et al. |
| 2014/0276096 A1 | 9/2014 | Bonutti |
| 2014/0324459 A1 | 10/2014 | Barfield |
| 2014/0340221 A1 | 11/2014 | Yuen et al. |
| 2014/0346158 A1 | 11/2014 | Matthews |
| 2014/0375452 A1 | 12/2014 | Yuen et al. |
| 2014/0375470 A1 | 12/2014 | Malveaux |
| 2014/0378872 A1 | 12/2014 | Hong et al. |
| 2015/0057512 A1 | 2/2015 | Kapoor |
| 2015/0065889 A1* | 3/2015 | Gandelman ........ A61B 5/02427 |
| | | 600/479 |
| 2015/0085245 A1 | 3/2015 | Howell et al. |
| 2015/0088464 A1 | 3/2015 | Yuen et al. |
| 2015/0148636 A1* | 5/2015 | Benaron ............... A61B 5/0059 |
| | | 600/328 |
| 2015/0173631 A1 | 6/2015 | Richards et al. |
| 2015/0179050 A1 | 6/2015 | Katingari et al. |
| 2015/0185506 A1 | 7/2015 | Lewis |
| 2015/0212329 A1 | 7/2015 | Sugihara et al. |
| 2015/0223805 A1 | 8/2015 | Whitman et al. |
| 2015/0244910 A1 | 8/2015 | Marston et al. |
| 2015/0281879 A1 | 10/2015 | Saadi |
| 2015/0287338 A1 | 10/2015 | Wells et al. |
| 2015/0332149 A1 | 11/2015 | Kolb et al. |
| 2015/0342482 A1 | 12/2015 | Carrara |
| 2015/0366518 A1 | 12/2015 | Sampson |
| 2016/0007849 A1 | 1/2016 | Krueger |
| 2016/0034042 A1 | 2/2016 | Joo |
| 2016/0041404 A1 | 2/2016 | Palermo et al. |
| 2016/0041613 A1 | 2/2016 | Klanner et al. |
| 2016/0066848 A1* | 3/2016 | Klosinski, Jr. ........ A61B 5/6803 |
| | | 600/301 |
| 2016/0117937 A1 | 4/2016 | Penders et al. |
| 2016/0199002 A1* | 7/2016 | Lee ...................... A61B 5/0008 |
| | | 340/870.07 |
| 2016/0223577 A1* | 8/2016 | Klosinski, Jr. ............. G01P 3/50 |
| 2016/0314468 A1 | 10/2016 | Smith et al. |
| 2017/0071528 A1 | 3/2017 | Chen |
| 2017/0255029 A1* | 9/2017 | Klosinski, Jr. ......... G02C 11/10 |
| 2017/0265798 A1* | 9/2017 | Sales ..................... A61B 5/18 |
| 2017/0323584 A1 | 11/2017 | Daniel et al. |
| 2018/0014737 A1* | 1/2018 | Paulussen ............ A61B 5/0037 |
| 2018/0064399 A1* | 3/2018 | Buettgen .............. G06K 9/2036 |
| 2018/0081201 A1* | 3/2018 | Lore .................. A61B 5/02438 |
| 2019/0216340 A1* | 7/2019 | Holz .................... A61B 5/0017 |

FOREIGN PATENT DOCUMENTS

| | | |
|---|---|---|
| WO | 2005015163 | 2/2005 |
| WO | 2005094667 | 10/2005 |
| WO | 2007088374 | 8/2007 |
| WO | 2008073806 | 6/2008 |
| WO | 2010006370 | 1/2010 |
| WO | 2010062479 | 6/2010 |
| WO | 2010062481 | 6/2010 |
| WO | 2011086466 | 7/2011 |
| WO | 2012041485 | 4/2012 |
| WO | 2013188343 | 12/2013 |
| WO | 2014021602 | 2/2014 |

(56) References Cited

FOREIGN PATENT DOCUMENTS

| WO | 2014108481 | 7/2014 |
| --- | --- | --- |
| WO | 2014144918 | 9/2014 |
| WO | 2014144940 | 9/2014 |
| WO | 2014170280 | 10/2014 |
| WO | 2014188244 | 11/2014 |
| WO | 2015015025 | 2/2015 |
| WO | 2015081299 | 6/2015 |
| WO | 2015095924 | 7/2015 |
| WO | 2015127143 | 8/2015 |
| WO | 2015127441 | 8/2015 |
| WO | 2016017997 | 2/2016 |
| WO | 2016029803 | 3/2016 |

OTHER PUBLICATIONS

Final Office Action, dated Dec. 11, 2018, from corresponding U.S. Appl. No. 14/610,501.
Office Action, dated Dec. 15, 2016, from corresponding U.S. Appl. No. 14/506,249.
Office Action, dated Dec. 31, 2018, from corresponding U.S. Appl. No. 14/550,406.
Office Action, dated Jan. 14, 2019, from corresponding U.S. Appl. No. 14/578,039.
Office Action, dated Jan. 14, 2019, from corresponding U.S. Appl. No. 15/060,333.
Office Action, dated Jul. 10, 2017, from corresponding U.S. Appl. No. 14/846,401.
Office Action, dated Jul. 18, 2019, from corresponding U.S. Appl. No. 14/846,401.
Office Action, dated Jun. 14, 2018, from corresponding U.S. Appl. No. 15/074,679.
Office Action, dated Jun. 30, 2017, from corresponding U.S. Appl. No. 14/610,589.
Office Action, dated Mar. 2, 2018, from corresponding U.S. Appl. No. 15/060,333.
Office Action, dated Mar. 29, 2017, from corresponding U.S. Appl. No. 14/562,454.
Office Action, dated Mar. 30 2018, from corresponding U.S. Appl. No. 14/846,401.
Final Office Action, dated May 23, 2017, from corresponding U.S. Appl. No. 14/578,039.
Final Office Action, dated Nov. 16, 2017, from corresponding U.S. Appl. No. 14/610,628.
Final Office Action, dated Sep. 25, 2018, from corresponding U.S. Appl. No. 14/610,439.
Final Office Action, dated Sep. 26, 2016, from corresponding U.S. Appl. No. 14/610,628.
International Preliminary Report on Patentability, dated Mar. 16, 2017, from corresponding International Application No. PCT/US2015/048612.
International Preliminary Report on Patentability, dated Mar. 16, 2017, from corresponding International Application No. PCT/US2015/048656.
International Preliminary Report on Patentability, dated Mar. 16, 2017, from corresponding International Application No. PCT/US2015/048662.
International Search Report, dated Dec. 18, 2015, from corresponding International Application No. PCT/US2015/048662.
International Search Report, dated Jan. 21, 2016, from corresponding International Application No. PCT/US2015/048612.
International Search Report, dated Jan. 21, 2016, from corresponding International Application No. PCT/US2015/048656.
International Search Report, dated Jun. 2, 2016, from corresponding International Application No. PCT/US2016/015705.
Invitation to Pay Additional Search Fees, dated Apr. 1, 2016, from corresponding International Application Serial No. PCT/US2016/015705.
Invitation to Pay Additional Search Fees, dated Nov. 4, 2015, from corresponding International Application Serial No. PCT/US2015/048612.
Invitation to Pay Additional Search Fees, dated Nov. 4, 2015, from corresponding International Application Serial No. PCT/US2015/048656.
Jeannet, Pierre-Yves, et al., "Continuous monitoring and quantification of multiple parameters of daily physical activity in ambulatory Duchenne muscular , dystrophy patients", Official Journal of the European Paediatric Neurology Society, 2011.
Maria S. Redin, "Marathon Man", Article Jun. 15, 1998, MIT Media Laboratory.
Michael Franco, Tzoa wearable turns you into a walking air-quality sensor, Dec. 9, 2014, CNET, https://www.cnet.com/news/tzoa-wearable-turns-you-into-a-walking-air-quality-sensor/.
Notice of Allowance, dated Dec. 13, 2017, from corresponding U.S. Appl. No. 14/610,501.
Notice of Allowance, dated Feb. 28, 2017, from corresponding U.S. Appl. No. 14/588,122.
Notice of Allowance, dated Jan. 17, 2019, from corresponding U.S. Appl. No. 14/610,439.
Notice of Allowance, dated Jul. 31, 2019, from corresponding U.S. Appl. No. 16/284,615.
Notice of Allowance, dated Jun. 21, 2017, from corresponding U.S. Appl. No. 14/562,454.
Notice of Allowance, dated Jun. 5, 2019, from corresponding U.S. Appl. No. 14/550,406.
Notice of Allowance, dated Oct. 11, 2018, from corresponding U.S. Appl. No. 15/074,679.
Notice of Allowance, dated Oct. 20, 2017, from corresponding U.S. Appl. No. 15/489,147.
Notice of Allowance, dated Sep. 13, 2018, from corresponding U.S. Appl. No. 15/594,898.
Office Action, dated Apr. 4, 2019, from corresponding U.S. Appl. No. 16/284,615.
Office Action, dated Aug. 19, 2016, from corresponding U.S. Appl. No. 14/578,039.
Office Action, dated Aug. 6, 2019, from corresponding U.S. Appl. No. 16/429,480.
Office Action, dated Aug. 7, 2018, from corresponding U.S. Appl. No. 14/550,406.
Office Action, dated Aug. 7, 2019, from corresponding U.S. Appl. No. 15/611,574.
Office Action, dated Dec. 29, 2016, from corresponding U.S. Appl. No. 14/610,589.
Office Action, dated Feb. 10, 2017, from corresponding U.S. Appl. No. 14/846,401.
Office Action, dated Feb. 11, 2019, from corresponding U.S. Appl. No. 14/846,401.
Office Action, dated Jan. 11, 2018, from corresponding U.S. Appl. No. 15/074,679.
Office Action, dated Jul. 1, 2016, from corresponding U.S. Appl. No. 14/562,454.
Office Action, dated Jul. 22, 2016, from corresponding U.S. Appl. No. 14/506,249.
Notice of Allowance, dated Sep. 11, 2019, from corresponding U.S. Appl. No. 16/259,646.
Action, dated Jul. 26, 2019, from corresponding U.S. Appl. No. 16/259,646.
Action, dated Jun. 11, 2019, from corresponding U.S. Appl. No. 14/610,501.
Action, dated Jun. 27, 2017, from corresponding U.S. Appl. No. 15/060,333.
Action, dated Jun. 27, 2019, from corresponding U.S. Appl. No. 15/060,333.
Action, dated Jun. 29, 2017, from corresponding U.S. Appl. No. 15/489,147.
Action, dated Jun. 8, 2018, from corresponding U.S. Appl. No. 14/610,501.
Action, dated Mar. 21, 2019, from corresponding U.S. Appl. No. 16/259,646.
Action, dated Mar. 3, 2017, from corresponding U.S. Appl. No. 14/610,628.

(56) References Cited

OTHER PUBLICATIONS

Action, dated Mar. 8, 2016, from corresponding U.S. Appl. No. 14/610,628.
Action, dated Mar. 9, 2018, from corresponding U.S. Appl. No. 14/610,439.
Action, dated May 23, 2018, from corresponding U.S. Appl. No. 14/578,039.
Office Action, dated Nov. 30, 2017, from corresponding U.S. Appl. No. 14/550,406.
Office Action, dated Oct. 4, 2018, from corresponding U.S. Appl. No. 15/191,196.
Office Action, dated Sep. 11, 2018, from corresponding U.S. Appl. No. 15/060,333.
Office Action, dated Sep. 2, 2016, from corresponding U.S. Appl. No. 14/588,122.
Office Action, dated Sep. 26, 2017, from corresponding U.S. Appl. No. 14/846,401.
Office Action, dated Sep. 29, 2017, from corresponding U.S. Appl. No. 14/506,249.
Phend, Crystal, "Calorie Intake Rises as Sleep Time Drops," Medpage Today, Medpage Today, LLC, Mar. 15, 2012, Web Dec. 19, 2016, http://www.medpagetoday.com/cardiology/prevention/31663.
Restriction Requirement, dated Nov. 10, 2016, from corresponding U.S. Appl. No. 14/846,401.
Restriction Requirement, dated Oct. 4, 2017, from corresponding U.S. Appl. No. 14/610,439.
Restriction Requirement, dated Sep. 13, 2017, from corresponding U.S. Appl. No. 14/550,406.
Richard M. Satava, et al., "The Physiologic Cipher at Altitude: Telemedicine and Real-Time Monitoring of Climbers on Mount Everest", Telemedicine Journal and e-Health, vol. 6, No. 3, 2000, Mary Ann Liebert, Inc.
Shankland, Stephen, "Google's electronic eyewear get 'OK Glass' voice commands", Feb. 20, 2013, Cnet.com, https://www.cnet.com/news/googles-electronic-eyewear-gets-ok-glass-voice-commands/.
Ted Burnham, Wearable Air Quality Sensor: Tzoa, Jan. 5, 2015, Postscapes, http://www.postscapes.com/wearable-air-quality-sensor-tzoa/.
Tolentino, Mellisa, Udderly Clever Wearable Tech Solutions, http://siliconangle.com/blog/2014/03/25/udderly-clever-wearable-tech-solutions/, Mar. 25, 2014.
Torres, Juan Carlos, ODG R-7 Smart Glasses Carries Its Own Android Inside, http://androidcommunity.com/odg-r-7-smart-glasses-carries-its-own-android-inside-20140919/, Sep. 19, 2014.
Written Opinion of the International Searching Authority, dated Dec. 18, 2015, from corresponding International Application No. PCT/US2015/048662.
Written Opinion of the International Searching Authority, dated Jan. 21, 2016, from corresponding International Application No. PCT/US2015/048612.
Written Opinion of the International Searching Authority, dated Jan. 21, 2016, from corresponding International Application No. PCT/US2015/048656.
Written Opinion of the International Searching Authority, dated Jun. 2, 2016, from corresponding International Application No. PCT/US2016/015705.
Notice of Allowance, dated Jan. 15, 2020, from corresponding U.S. Appl. No. 16/429,480.
Notice of Allowance, dated Dec. 11, 2019, from corresponding U.S. Appl. No. 15/611,574.
Office Action, dated Oct. 4, 2019, from corresponding U.S. Appl. No. 15/791,196.
Office Action, dated May 7, 2020, from corresponding U.S. Appl. No. 16/657,982.
Office Action, dated Jun. 11, 2020, from corresponding U.S. Appl. No. 16/449,759.

* cited by examiner

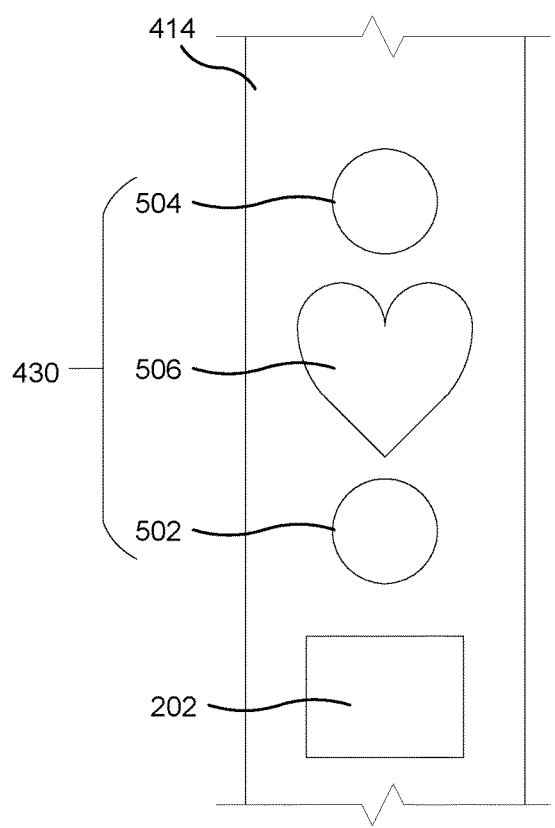
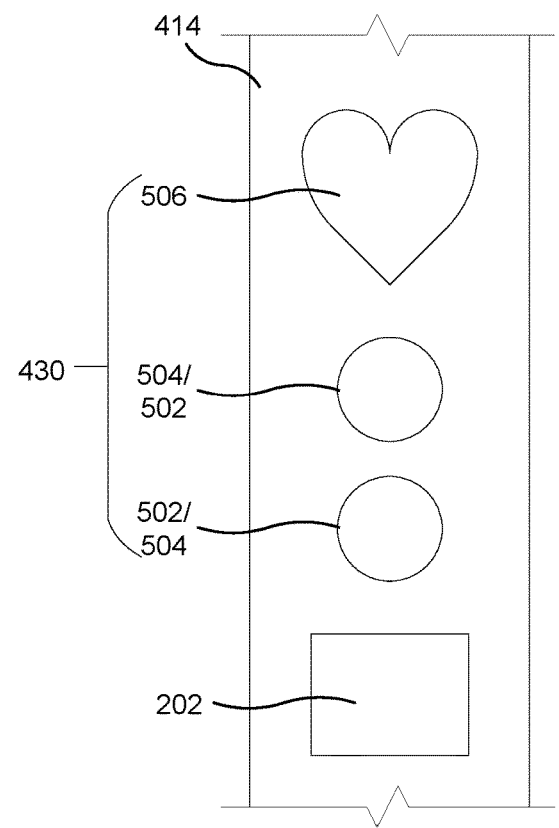
FIG. 5A
FIG. 5B

HEART RATE DETECTION SYSTEM AND METHOD

CROSS REFERENCE TO RELATED APPLICATIONS

This application claims the benefit of U.S. Provisional Patent Application Ser. No. 62/713,493, filed Aug. 1, 2018, and entitled "Heart Rate Detection System and Method," the entire disclosure of which is incorporated by reference herein in its entirety.

BACKGROUND

Heart rate detection and monitoring is an important process for many individuals. Heart rate monitoring can be desirable for both medical and fitness purposes. Individuals with medical issues related to the heart need to closely monitor their heart rates to ensure that the results do not fall outside of a prescribed range. Similarly, many individuals wear heart monitors while working out or participating in sports. Doing so allows the individual to alter their activity to optimize their heart rate for providing the maximum physical fitness benefits, as well as or alternatively to avoid over-stressing their heart.

There are many types of heart rate monitors available to consumers. Most are very bulky and cumbersome. For example, many conventional heart rate monitors include a strap that must be accurately placed around the individual's chest and worn during monitoring. The strap communicates wirelessly with a separate device that is typically worn on the individual's wrist, e.g., interfacing with a watch or bike computer. These types of devices are uncomfortable and require multiple components to be worn or used by the individual.

Other conventional heart rate monitors attempt to utilize photodiodes and LEDs that contact a person's skin (e.g., mounted on a rear side of a watch or device worn on a person's wrist) to measure the light absorption in the blood flowing through the wrist. Because these types of monitors require continuous skin contact, these measurements are often inaccurate as the device bounces around, moves, or encounters sweat or dirt.

Accordingly, there is a need for improved systems and methods that address these and other needs.

SUMMARY

According to various embodiments, computerized eyewear includes a frame, a first temple, a second temple, and a processor. The frame has a frame first end and a frame second end. The first temple has a first temple first end that is pivotally coupled to the frame first end and a first temple second end that is configured to rest on a first ear of a wearer of the computerized eyewear. The second temple has a second temple first end that is pivotally coupled to the frame second end and a second temple second end that is configured to rest on a second ear of a wearer of the computerized eyewear. A first optical sensor is at least partially embedded in the second temple and operative to transmit a first signal to a temple of the wearer of the computerized eyewear to measure a raw heart rate delta. A second optical sensor is at least partially embedded in the second temple proximate to the first optical sensor and operative to transmit a second signal to the temple of the wearer of the computerized eyewear to measure a noise delta. The processor is coupled to one of the first temple, the second temple, or the frame and communicatively coupled to the first optical sensor and the second optical sensor. The processor is operative to use the first signal to generate the raw heart rate delta, to use the second signal to generate the noise delta, and to use the raw heart rate delta and the noise delta to determine a measured heart rate of the wearer of the computerized eyewear.

According to other embodiments, a computer-implemented method for measuring a heart rate of a wearer of computerized eyewear is provided. The method includes receiving a first signal from a first optical sensor at least partially embedded in an eyewear temple of the computerized eyewear. A raw heart rate delta is determined from the first signal. A second signal is received from a second optical sensor at least partially embedded in an eyewear temple of the computerized eyewear proximate to the first optical sensor. A noise delta is determined from the second signal. A measured heart rate of the wearer of the computerized eyewear is determined using the raw heart rate delta and the noise delta.

According to yet other embodiments, computerized eyewear includes a frame, an eyewear temple pivotally coupled to the frame, and a processor. The eyewear temple includes a first optical sensor and a second optical sensor. The first optical sensor is at least partially embedded in the eyewear temple and is operative to transmit a first signal to a temple of the wearer of the computerized eyewear to measure a raw heart rate delta. The second optical sensor is at least partially embedded in the eyewear temple and is operative to transmit a second signal to the temple of the wearer of the computerized eyewear to measure a noise delta. The processor is communicatively coupled to the first optical sensor and the second optical sensor. The processor is operative to use the first signal to generate the raw heart rate delta, to use the second signal to generate the noise delta, and to use the raw heart rate delta and the noise delta to determine a measured heart rate of the wearer of the computerized eyewear

BRIEF DESCRIPTION OF THE DRAWINGS

Various embodiments of systems and methods for detecting a heart rate are described below. In the course of this description, reference will be made to the accompanying drawings, which are not necessarily drawn to scale and wherein:

FIGS. 5A and 5B are top views of a portion of a temple of an eyewear showing alternative configurations of a heart rate detection system according to various embodiments.

DETAILED DESCRIPTION OF SOME EMBODIMENTS

Figure 1:
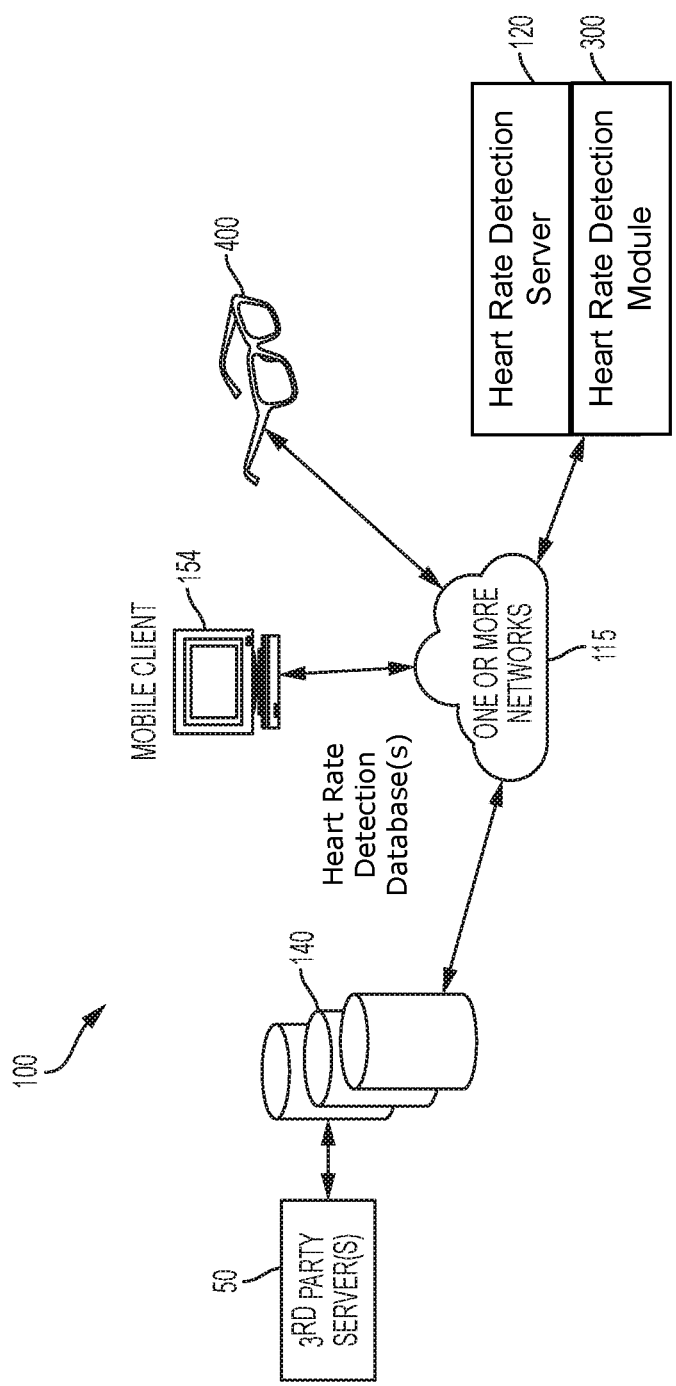
FIG. 1 is a block diagram of a heart rate detection system in accordance with an embodiment of the present system.

Various embodiments will now be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

As a person's heart beats, the heart contracts, forcing blood at a high pressure through the person's arteries. In response to these high pressure surges, the arteries expand outward in diameter. As the flow of blood subsides in between beats, the arteriel walls contract inward. As a result of this process, the skin adjacent to a large artery may visibly pulse outward in rhythm with the heart rate of the individual. In various embodiments, a wearable heart rate detection system may measure the distance between the sensor and the skin of the wearer. The difference in the distance over time is representative of the heart rate of the wearer. This difference in the distance between the sensor and the skin of the wearer over time will be referred to herein as the "delta." For the purposes of this disclosure, the delta that includes the heartbeat of the wearer will be referred to as the "raw heart rate delta." When the wearer is perfectly still, without any movement, the raw heart rate delta will purely represent the heart rate of the wearer since the raw heart rate delta is completely caused by the pulsation of the wearer's artery as it expands and contracts with the heartbeat.

However, a complication with accurately measuring a heart rate by optically measuring a delta is that factors other than heart rate often create or alter this measurement. For example, a prime location for measuring the delta is at a person's temple. The superficial temporal artery traverses the area adjacent a person's temple, so the pulsing of the artery creates a measurable delta at the temple. However, the temple is also an area in which various bones and muscles of the human anatomy come together under the skin. As a result, various movements of a person's mouth (e.g., chewing, biting, teeth grinding, talking, and yawning), ears, or even neck muscles may create a delta at the temple that may interfere with measuring a heart rate. Moreover, eyewear or other wearable devices possessing the sensors for measuring the delta are subject to movement as the wearer walks, runs, turns his or her head, and otherwise moves around. For the purposes of this disclosure, the delta that is caused by, or substantially caused by, movement and factors other than the heartbeat of the wearer will be referred to as the "noise delta."

Utilizing the concepts and technologies described herein, these challenges are overcome through the use of at least two sensors embedded in or mounted to a temple of eyewear. This disclosure describes the various embodiments in the context of the heart rate detection system being embedded or mounted on eyewear. However, it should be appreciated, that the various components and concepts described herein may be used with any wearable device (e.g., a watch, a helmet, a headband, a wristband, goggles, a hat or other headwear), and are not limited to use with eyewear.

According to various embodiments, one optical sensor is positioned within the temple of the eyewear such that the sensor has a narrow field of detection focused on the optimum position at the wearer's temple in which the delta from the heartbeat of the wearer may be measured. This area of the wearer's temple will be referred to as the "heart rate detection area." A second optical sensor is positioned proximate to the first optical sensor and is configured with a wider field of detection that is larger than the heart rate detection area. According to one embodiment, the second sensor is positioned just forward of the first optical sensor to capture a larger area of the wearer's temple. This wider field of detection, while it may encompass the heart rate detection area, is not focused soley on the superficial temporal artery. As the wearer moves, chews, speaks, etc, the wide focus area of the second sensor expands and contracts. As a result, the delta measured in the larger field of detection is a noise delta since it is primarily influenced by movement and factors other than the heartbeat of the wearer. This second, larger area of the wearer's temple that is used to measure the noise delta will be referred to as the "noise detection area."

According to embodiments described herein, the at least two sensors of the heart rate detection system measure the raw heart rate delta and the noise delta, scale and subtract these measurements, which results in a measured heart rate delta that primarily includes the heart rate of the wearer.

In various embodiments, the system includes at least two optical sensors coupled to the wearable device. The sensors may be coupled to the wearable device in any suitable way. For instance, the one or more sensors may be embedded into the wearable device, coupled to the wearable device, and/or operatively coupled to the wearable device. According to one illustrative embodiment, the system includes two sensors embedded within a temple of eyewear. Each optical sensor may include an LED and a detector, or an LED operatively coupled to a detector such that the time is measurable between illumination of the LED and detection of the reflection of the light by the detector.

According to embodiments, the two optical sensors include two LEDs that share a single detector. The detector may include a photodiode configured to convert light into an electrical current. After light is emitted from the LED, the light is reflected back by the skin on the temple of the wearer. The reflected light is received by the photodiode and converted into an electrical current. A processor coupled to the optical sensor measures the time-delay of the light from the LED to the temple and back to the photodiode. Using the speed of light and this time-delay, the processor may determine the distance between the optical sensor and the temple of the wearer. This distance measured over time creates the raw heart rate delta and the noise delta from the two sensors. After scaling and subtracting these measurements, the measured heart rate is determined. According to one embodiment, the sensors include a 24-bit analog-to-digital converter (ADC) that is close to the photodiode. This configuration allows for signaling that is clean, with a dynamic range of over 16 bits for use within a wide range of lighting conditions, from very bright sunlight to a dark room.

Exemplary Technical Platforms

As will be appreciated by one skilled in the relevant field, the present systems and methods may be, for example, embodied as a computer system, a method, or a computer program product. Accordingly, various embodiments may be entirely hardware or a combination of hardware and software. Furthermore, particular embodiments may take the form of a computer program product stored on a computer-readable storage medium having computer-readable instructions (e.g., software) embodied in the storage medium. Various embodiments may also take the form of Internet-implemented computer software. Any suitable computer-readable storage medium may be utilized including, for example, hard disks, compact disks, DVDs, optical storage devices, and/or magnetic storage devices.

Various embodiments are described below with reference to block diagram and flowchart illustrations of methods, apparatuses, (e.g., systems), and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a general purpose computer, a special purpose computer, or other programmable data processing apparatus that can direct a computer or other programmable data processing apparatus to function in a particular manner such that the instructions stored in the computer-readable memory produce an article of manufacture that is configured for implementing the functions specified in the flowchart block or blocks.

The computer instructions may execute entirely on the user's computer, partly on the user's computer, as a stand-alone software package, partly on a user's computer and partly on a remote computer, or entirely on the remote computer or server. In the latter scenario, the remote computer may be connected to the user's computer through any suitable type of network, including but not limited to: a local area network (LAN); a wide area network (WAN), such as the Internet; and/or a cellular network.

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer-implemented process (e.g., method) such that the instructions that execute on the computer or other programmable apparatus provide steps for implementing the functions specified in the flowchart block or blocks.

Example System Architecture

FIG. 1 is a block diagram of a Heart Rate Detection System 100 according to particular embodiments. As may be understood from this figure, the Heart Rate Detection System 100 includes One or More Networks 115, One or More Third Party Servers 50, a Heart Rate Detection Server 120 that may, for example, be adapted to execute a Heart Rate Detection Module 300, one or more Databases 140, one or more Remote Computing Devices 154 (e.g., a smart phone, a tablet computer, a wearable computing device, a laptop computer, a desktop computer, etc.), and one or more Heart Rate Detection Devices 400, which may, for example, be embodied as eyewear, headwear, clothing, a watch, a hat, a helmet, a cast, an adhesive bandage, a piece of jewelry (e.g., a ring, earring, necklace, bracelet, brooch, etc.), or any other suitable wearable device or other device (e.g., other computing device). In particular embodiments, the one or more computer networks 115 facilitate communication between the One or More Third Party Servers 50, the Heart Rate Detection Server 120, the one or more Databases 140, the one or more Remote Computing Devices 154, and the one or more Heart Rate Detection Devices 400.

The one or more networks 115 may include any of a variety of types of wired or wireless computer networks such as the Internet (or other WAN), a private intranet, a mesh network, a public switch telephone network (PSTN), and/or any other type of network (e.g., a network that uses Bluetooth or near field communications to facilitate communication between computing devices). The communication link between the One or More Remote Computing Devices 154 and the Heart Rate Detection Server 120 may be, for example, implemented via a Local Area Network (LAN) or via the Internet (or other WAN).

Figure 2:
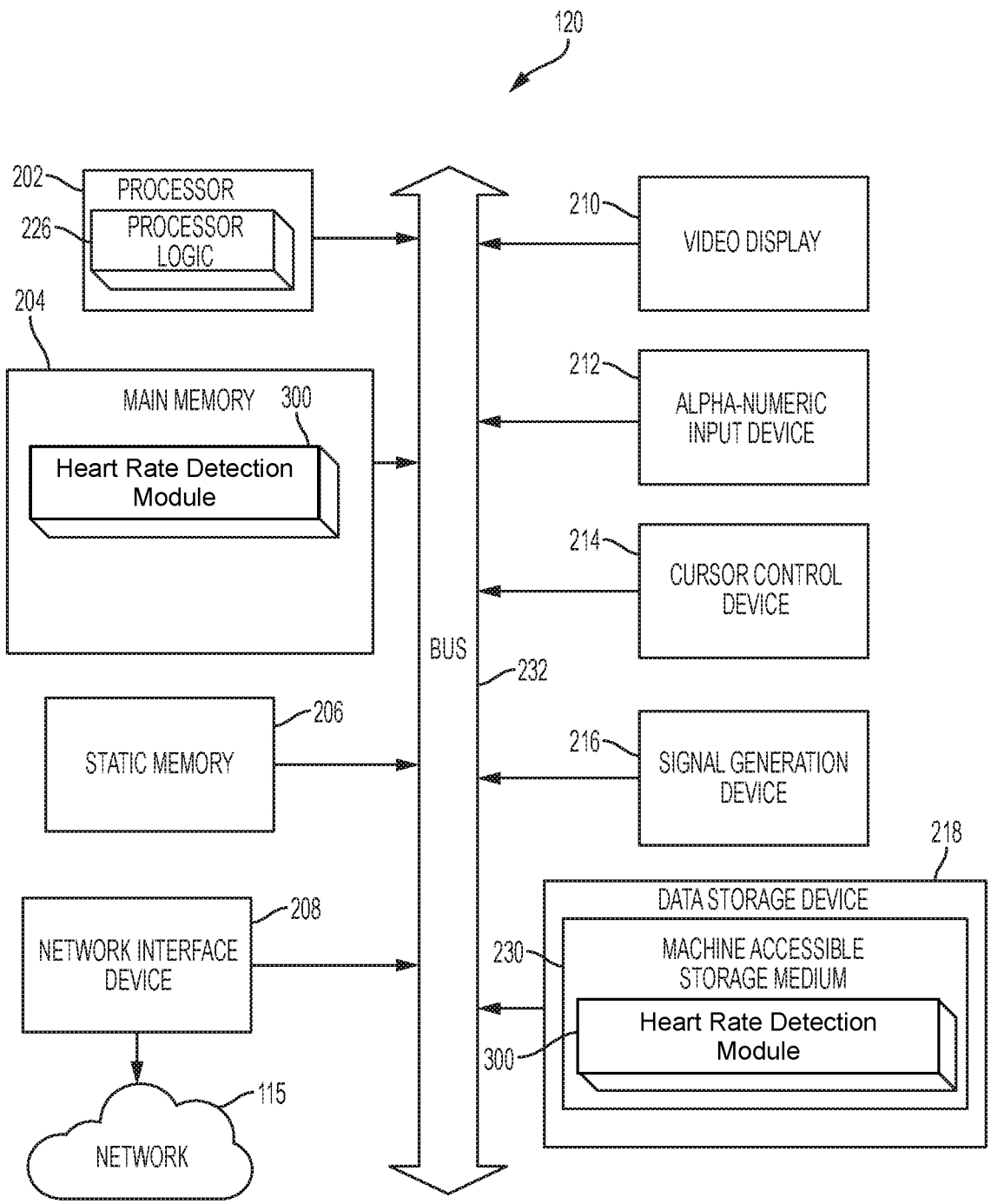
FIG. 2 is a block diagram of the heart rate detection server of FIG. 1.

FIG. 2 illustrates a diagrammatic representation of an exemplary architecture of a Heart Rate Detection Server 120 that may be used within various embodiments of the Heart Rate Detection System 100. It should be understood that the computer architecture shown in FIG. 2 may also represent the computer architecture for any one of the one or more Remote Computing Devices 154, one or more Third Party Servers 50, and/or the one or more Heart Rate Detection Devices 400 shown in FIG. 1. In particular embodiments, the Heart Rate Detection Server 120 may be suitable for use as a computer within the context of the Heart Rate Detection System 100 that is configured to determine the heart rate of a wearer using one or more signals received from one or more sensors coupled to the one or more Heart Rate Detection Devices 400. In other particular embodiments, the Heart Rate Detection Device 400 may include an on-board computer processor that is adapted to execute a Heart Rate Detection Module 300 to determine the heart rate of the wearer.

In particular embodiments, the Heart Rate Detection Server 120 may be connected (e.g., networked) to other computing devices in a LAN, an intranet, an extranet, and/or the Internet as shown in FIG. 1. As noted above, the Heart Rate Detection Server 120 may operate in the capacity of a server or a client computing device in a client-server network environment, or as a peer computing device in a peer-to-peer (or distributed) network environment. The Heart Rate Detection Server 120 may be a desktop personal computing device (PC), a tablet PC, a set-top box (STB), a Personal Digital Assistant (PDA), a smartphone, a web appliance, a network router, a switch or bridge, or any other computing device capable of executing a set of instructions (sequential or otherwise) that specify actions to be taken by that computing device. Further, while only a single computing device is illustrated, the term "computing device" shall also be interpreted to include any collection of computing devices that individually or jointly execute a set (or multiple sets) of instructions to perform any one or more of the methodologies discussed herein, or other suitable methodologies.

As shown in FIG. 2, an exemplary Heart Rate Detection Server 120 includes a processing device 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processing device 202 represents one or more general-purpose or specific processing devices such as a microprocessor, a central processing unit (CPU), or the like. More particularly, the processing device 202 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. The processing device 202 may also be one or more special-purpose processing devices such as an application specific integrated circuit (ASIC), a field programmable gate array (FPGA), a digital signal processor (DSP), network processor, or the like. The processing device 202 may be configured to execute processing logic 226 for performing various operations and steps discussed herein.

The Heart Rate Detection Server 120 may further include a network interface device 208. The Heart Rate Detection Server 120 may also include a video display unit 210 (e.g., a liquid crystal display (LCD) or a cathode ray tube (CRT)), an alpha-numeric input device 212 (e.g., a keyboard), a cursor control device 214 (e.g., a mouse), a signal generation device 216 (e.g., a speaker), and a data storage device 218.

The data storage device 218 may include a non-transitory computing device-accessible storage medium 230 (also known as a non-transitory computing device-readable storage medium, a non-transitory computing device-readable medium, or a non-transitory computer-readable medium) on which is stored one or more sets of instructions (e.g., the Heart Rate Detection Module 300) embodying any one or more of the methodologies or functions described herein. The one or more sets of instructions may also reside, completely or at least partially, within the main memory 204 and/or within the processing device 202 during execution thereof by the Heart Rate Detection Server 120—the main memory 204 and the processing device 202 also constituting computing device-accessible storage media. The one or more sets of instructions may further be transmitted or received over a network 115 via a network interface device 208.

While the computing device-accessible storage medium 230 is shown in an exemplary embodiment to be a single medium, the term "computing device-accessible storage medium" should be understood to include a single medium or multiple media (e.g., a centralized or distributed database, and/or associated caches and servers) that store the one or more sets of instructions. The term "computing device-accessible storage medium" should also be understood to include any medium that is capable of storing, encoding, or carrying a set of instructions for execution by the computing device and that causes the computing device to include any one or more of the methodologies of the present invention. The terms "computing device-accessible storage medium" and like terms should accordingly be understood to include, but not be limited to, solid-state memories, optical and magnetic media, etc.

Exemplary Heart Rate Detection Device

Figure 4:
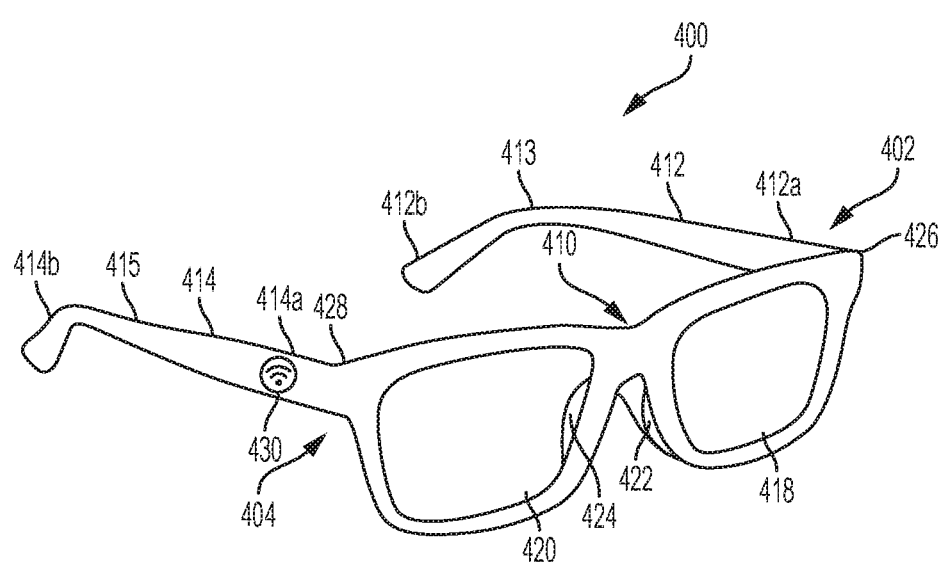
FIG. 4 is an exemplary wearable heart rate detection device for use in the heart rate detection system of FIG. 1.

As shown in FIG. 1, the Heart Rate Detection System 100, in various embodiments, comprises one or more Heart Rate Detection Devices 400. A particular embodiment of a heart rate detection device is shown in FIG. 4 as eyewear 400. As shown in this figure, eyewear 400, according to various embodiments, includes: (1) an eyewear frame 410; (2) a first temple 412; and (3) a second temple 414. These various components are discussed in more detail below.

Eyewear Frame

Referring still to FIG. 4, eyewear 400, in various embodiments, includes any suitable eyewear frame 410 that is configured to support one or more lenses 418, 420. In the embodiment shown in this figure, the eyewear frame 410 defines a first end 402 and a second end 404. The eyewear frame 410 may be made of any suitable material such as metal, ceramic, one or more polymers or any combination thereof. In particular embodiments, the eyewear frame 410 is configured to support the first and second lenses 418, 420 about the full perimeter of the first and second lenses 418, 420. In other embodiments, the eyewear frame 410 may be configured to support the first and second lenses 418, 420 about only a portion of each respective lens. In various embodiments, the eyewear frame 410 is configured to support a number of lenses other than two lenses (e.g., a single lens, a plurality of lenses, etc.). In particular embodiments, the lenses 418, 420 may include prescription lenses, sunglass lenses, or any other suitable type of lens (e.g., reading lenses, non-prescription lenses), which may be formed from glass or a suitable polymer.

In various embodiments, the eyewear frame 410 includes a first and second nose pad 422, 424, which may be configured to maintain the eyewear 400 adjacent the front of a wearer's face such that the lenses 418, 420 are positioned substantially in front of the wearer's eyes while the wearer is wearing the eyewear 400. In particular embodiments, the nose pads 422, 424 may comprise a material that is configured to be comfortable when worn by the wearer (e.g., rubber, plastic, etc.). In other embodiments, the nose pads 422, 424 may include any other suitable material (e.g., metal, etc.). In still other embodiments, the nose pads 422, 424 may be integrally formed with the frame 410.

The eyewear frame 410 includes a first and second hinge 426, 428 that attach the first and second temples 412, 414 to the frame first and second ends 402, 404, respectively. In various embodiments, the hinges 426, 428 may be formed by any suitable connection (e.g., tongue and groove, ball and socket, spring hinge, etc.). In particular embodiments, the first hinge 426 may be welded to, or integrally formed with, the frame 410 and the first temple 412, and the second hinge 428 may be welded to, or integrally formed with, the frame 410 and the second temple 414.

First and Second Temples

As shown in FIG. 4, the first temple 412, according to various embodiments, is rotatably connected to the frame 410 at a right angle to extend the first temple 412 substantially perpendicular, substantially parallel, or anywhere in between the right angle to the frame 410. The first temple 412 has a first and second end 412a, 412b. Proximate the first temple second end 412b, the first temple 412 includes an earpiece 413 configured to be supported by a wearer's ear. Similarly, the second temple 414, according to various embodiments, is rotatably connected to the frame 410 at a right angle to extend the second temple 414 substantially perpendicular, substantially parallel, or anywhere in between the right angle to the frame 410. The second temple 414 has a first and second end 414a, 414b. Proximate the second temple second end 414b, the second temple 414 includes an earpiece 415 configured to be supported by a wearer's ear.

Sensors

In various embodiments, one or more sensors 430 may be coupled to the frame 410, the first and second temples 412, 414, the first and second lenses 418, 420, or any other portion of the eyewear 400 in any suitable way. For instance, the one or more sensors 430 may be embedded into the eyewear 400, substantially permanently coupled to the eyewear 400 (e.g. using suitable welding or bonding techniques), and/or detachably coupled to the eyewear 400 (e.g. using a suitable spring-loaded clamp, etc.). In various embodiments, the one or more sensors 430 may be positioned at any point along the eyewear 400. For instance, a heart rate detection sensor may be disposed adjacent the first temple of the eyewear 400. Specifically, two heart rate detection sensors may be positioned within the first or second temple of the eyewear 400 at a position substantially adjacent the temple of wearer such that light may be emitted toward the wearer's temple at an approximate angle of 90 degrees from the temple of the eyewear.

FIGS. 5A and 5B show illustrative configurations of the Heart Rate Detection System 100 according to various embodiment. In these examples, a first sensor 502 and a second sensor 504 are embedded within a temple 414 of the eyewear 400. Only a portion of the temple 414 is shown for clarity purposes. The first sensor 502 includes a narrow field emitter or LED, while the second sensor 504 includes a wide field emitter or LED. The LEDs may be green or red, or any suitable color, including infrared. One with skill in the art would be able to select an appropriate LED or other emitter for use with the narrow and wide field implementations.

FIG. 5A will be described in detail. FIG. 5B includes the same components as those shown in FIG. 5A, but in different positions. FIG. 5B is shown to illustrate that the positioning of the various components of the Heart Rate Detection System 100 may be altered without departing from the scope of this disclosure. Looking now at FIG. 5A, according to one embodiment, the sensors 430 are embedded within the temple 412 of eyewear 400. The sensors 430 include a first sensor 502 that is a narrow field LED and a second sensor 504 that is a spread beam, or wide field LED that are approximately equidistant from and positioned on opposite sides of a detector 506. According to this embodiment, the detector 506 includes an aperture or orifice that is substantially shaped like a heart. While the heart-shaped aperture provides an aesthetic appeal to a heart rate detection system, the shape additionally provides a substantial advantage in the detection and analysis of the narrow and wide field signals from the sensors 430. This advantage will be discussed in detail below with respect to FIG. 3 and the Heart Rate Detection Module 300.

According to various embodiments, the detector 506 and/or the first and second sensors, 502 and 504, respectively, may include one or more lenses over the apertures encompassing the sensors 430. Lenses may be made from any suitable material and may be shaped and sized to focus the respective beams in a desirable manner. As an example, lenses may assist the configuration of the gradient signal emitted from the first sensor 502 and reflected back to the detector 506. Lenses may additionally assist in spreading the signal from the second sensor 504 across the temple of the wearer.

Exemplary System Platform

As noted above, a system, according to various embodiments, is adapted to monitor the heart rate of a wearer of a wearable device. Various aspects of the system's functionality may be executed by certain system modules, including the Heart Rate Detection Module 300. The Heart Rate Detection Module 300 is discussed in greater detail below.

Heart Rate Detection Module

Figure 3:
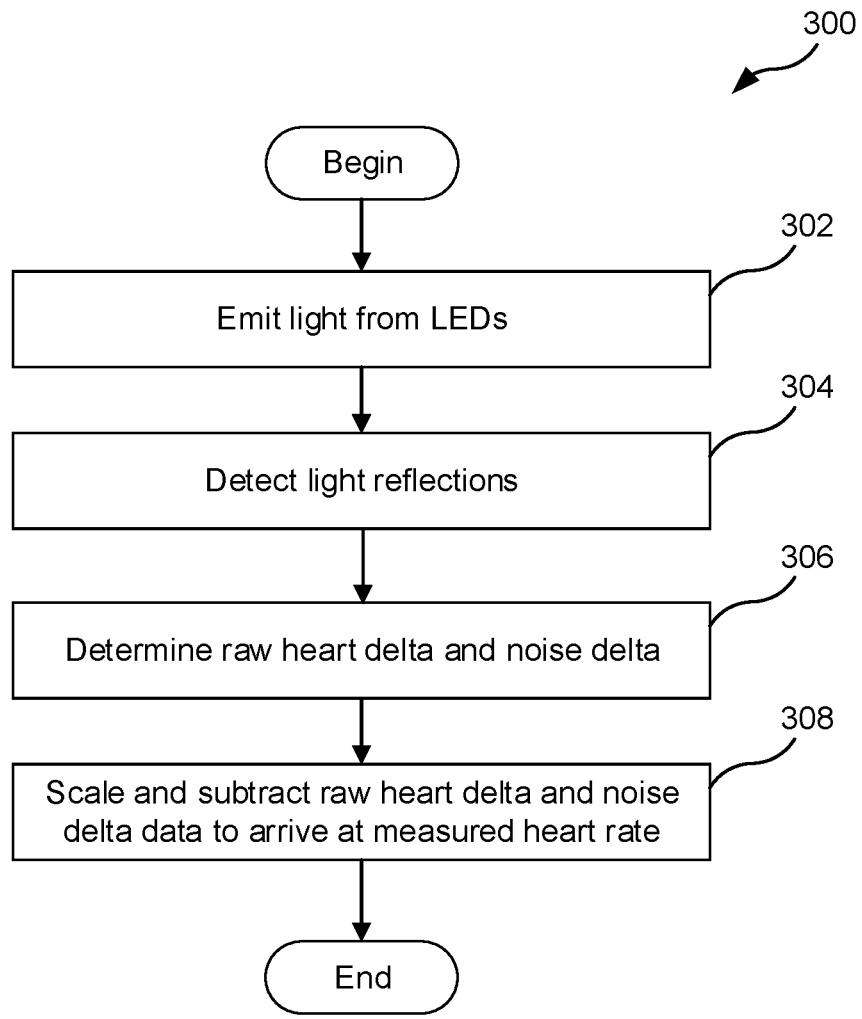
FIG. 3 depicts a flowchart that generally illustrates various steps executed by a heart rate detection module according to a particular embodiment.

FIG. 3 is a flow chart of operations 300 performed by an exemplary Heart Rate Detection Module 300, which may, for example, run on the Heart Rate Detection Server 120, or any other suitable computing device (such as the one or more Heart Rate Detection Devices 400). In various embodiments, the system begins, at operation 302 by emitting light from the sensors 430. Specifically, the narrow and wide field emitters are activated to emit light from LEDs to the surface of the wearer's skin on the temple. The heart rate detection and monitoring may be triggered by a command from the user, at pre-determined times or intervals, or upon detection of an event. For example, the user may provide a voice command that triggers the measurement and storage and/or reporting of the wearer's heartrate. Alternatively, the user may provide a hand gesture, head movement, or eye movement that is detected by a camera, motion sensor, or any other applicable sensor coupled to the eyewear. According to another example, gyroscopes, accelerometers, or other sensors may detect the beginning of an exercise event (e.g., the wearer starts to jog). This activity may trigger the measurement and storage and/or reporting of the wearer's heartrate. Similarly, the cessation of the activity may again activate the sensors 430 and corresponding measurement of the wearer's heartrate. The eyewear may be programmed to take measurements at predetermined time and/or distance intervals during an exercise event.

At operation 304, the detector 506 receives reflections of the light from the narrow and wide field LEDs. The raw heart delta and the noise delta are determined at operation 306. As discussed above, the narrow field light emitted from the first sensor 502 is focused on the heart rate detection area of the wearer's temple. The reflection of the light is detected. The change in the time delay between transmission and receipt of the reflection is indicative of the rate of change of the distance between the sensor and the surface of the wearer's temple as the heart beat deforms repeatedly deforms the temple outward toward the sensor and inward again as the blood pulses through the corresponding artery.

The light from the first sensor 502 is not only a narrow beam, but it also is a gradient towards the center of higher and higher density of light. Small fluctuations along the gradient are going to provide a non-linear signal, which is representative of the raw heart delta. In contrast, the wide field light emitted from the second sensor 504 is focused widely on the noise detection area, which is a larger area of the wearer's temple that is used to measure the noise delta. The noise detection area encompasses the heart rate detection area of the wearer's temple and a surrounding area. This wider field of light is even, without a gradient. As a result, the same deformation of the temple of the wearer will provide a linear signal. These two signals are scaled and subtracted to arrive at a measured heart rate delta that primarily includes the heart rate of the wearer.

The two signals from the first and second sensors 502 and 504, respectively, can be analyzed in various ways known to those with skill in the art to arrive at the measured heart rate. The results of a plurality of analysis methods can be averaged or subjected to known error correction techniques to determine the measured heart rate. By doing so, if one or both signals from the sensors 430 are lost during heart rate monitoring, the heart rate data may be extrapolated from the most recent data until the lost signal(s) are recovered.

The heart-shaped aperture of the detector 506 significantly enhances the signal differentiation and analysis process. The "V" portion of the bottom of the heart is adjacent to the first sensor 502 that provides the gradient signal. When the 50 percent line of the gradient travels upwards, providing a far more accentuated signal due to the V shape. In other words, the gradient line that is 50 percent of the power is at the bottom of the V. As it comes closer, the V orifice opens providing more power. So the V assists with the signal processing of the gradient signal from the narrow field emitter of sensor 502. On the other side of the detector 506, the second sensor 504 provides a flat surfaced signal with no gradient. "Looking" side-to-side at the bony structure of the temple without looking directly at the soft tissue over the superficial temporal artery provides the optimum noise detection area that provides a noise delta associated with movement not caused by the pulse of the wearer's heartbeat. To do so, light from the wide field emitter of sensor 504 may be thought of as being directed towards two circles adjacent to one another and encompassing the outer portions of the noise detection area, while providing a divider down the middle towards the heart rate detection area of the first sensor 502. This structure is represented by the two outer lobes of the heart, converging in the top center portion of the heart. Consequently, the heart-shaped aperture of the detector 506 shown in FIG. 5A significantly enhances the detection and accuracy of the heart rate delta and the noise delta, resulting in an accurate measured heart rate.

According to alternative embodiments, the detector 506 may include an aperture that is substantially circular, square, rectangular, or any other suitable shape. To create the desired configuration of the gradient signal emitted from the first sensor 502 and reflected back to the detector 506, lenses may be used, as described above. In these embodiments, a lens positioned over the aperture may be heart-shaped or otherwise shaped to enhance the performance of the detector, rather than the aperture itself being heart-shaped.

Conclusion

Many modifications and other embodiments of the invention will come to mind to one skilled in the art to which this invention pertains, having the benefit of the teaching presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. Computerized eyewear, comprising:
    a frame, wherein the frame comprises
        a frame first end, and
        a frame second end;
    a first temple, wherein the first temple comprises
        a first temple first end pivotally coupled to the frame first end, and
        a first temple second end configured to rest on a first ear of a wearer of the computerized eyewear;
    a second temple, wherein the second temple comprises
        a second temple first end pivotally coupled to the frame second end,
        a second temple second end configured to rest a second ear of the wearer of the computerized eyewear,
        a first optical transmitter at least partially embedded in the second temple and operative to transmit a first signal to a temple of the wearer of the computerized eyewear to measure a raw heart rate delta,
        a second optical transmitter at least partially embedded in the second temple proximate to the first optical transmitter and operative to transmit a second signal to the temple of the wearer of the computerized eyewear to measure a noise delta, and
        a detector at least partially embedded in the second temple proximate to the first optical transmitter and to the second optical transmitter, the detector operative to receive a reflected first signal originating from the first optical transmitter or a reflected second signal originating from the second optical transmitter and reflected back to the detector from a surface of the temple of the wearer;
    at least one processor coupled to one of the first temple, the second temple, or the frame and communicatively coupled to the first optical transmitter, the second optical transmitter, and the detector, the at least one processor operative to use the reflected first signal over time representative of a movement of a heart rate detection area of the surface of the temple of the wearer to generate the raw heart rate delta, to use the reflected second signal over time representative of a movement of a wide field of detection on the surface of the temple of the wearer that is larger than the heart rate detection area to generate the noise delta, and to use the raw heart rate delta and the noise delta to determine a measured heart rate of the wearer of the computerized eyewear.

2. The computerized eyewear of claim 1, wherein the first optical transmitter comprises a narrow field emitter operative to focus the first signal on the heart rate detection area of the temple of the wearer, the heart rate detection area comprising a superficial temporal artery of the wearer.

3. The computerized eyewear of claim 2, wherein the second optical transmitter comprises a wide field emitter operative to focus the second signal on the wide field of detection that is larger than the heart rate detection area of the first signal.

4. The computerized eyewear of claim 3, wherein the first optical transmitter comprises a narrow field emitting Light Emitting Diode (LED) and the second optical transmitter comprises a wide field emitting LED.

5. The computerized eyewear of claim 4, wherein the first optical transmitter and the second optical transmitter are positioned approximately equidistant from and on opposite sides of the detector.

6. The computerized eyewear of claim 5, wherein the detector comprises a heart-shaped aperture that is shaped like a heart to enhance detection or differentiation of the reflected first signal and the reflected second signal.

7. The computerized eyewear of claim 6, wherein the first optical transmitter is positioned proximate to a point of the heart-shaped aperture.

8. The computerized eyewear of claim 4, wherein the detector comprises a photodiode configured to convert light into an electrical current.

9. The computerized eyewear of claim 8, wherein the first optical transmitter comprises a narrow field emitting LED and the second optical transmitter comprises a wide field emitting LED, and wherein the processor is operative to
    measure the time-delay of the light from each LED to the temple and back to the photodiode,
    utilize the time-delay measurement to determine a first distance between the first optical transmitter and the temple and a second distance between the second optical transmitter and the temple,
    repeat the determination of the first distance over a period of time to determine the raw heart rate delta,
    repeat the determination of the second distance over the period of time to determine the noise delta, and
    isolate a heart rate from the raw heart rate delta and the noise delta to determine the measured heart rate of the wearer.

10. The computerized eyewear of claim 4, further comprising one or more lenses positioned over the detector, wherein the one or more lenses are configured to alter or focus the first signal, the second signal, the reflected first signal, or the reflected second signal.

11. The computerized eyewear of claim 10, wherein the one or more lenses are configured to spread the reflected second signal emitted from the second optical transmitter and reflected from the temple of the wearer.

12. The computerized eyewear of claim 11, wherein at least one of the one or more lenses is shaped like a heart.

13. A computer-implemented method for measuring a heart rate of a wearer of computerized eyewear, the method comprising:
    transmitting, from a first optical transmitter at least partially embedded in an eyewear temple of the computerized eyewear, a first signal to a heart rate detection area of the surface of the temple of the wearer to create a reflected first signal from the surface;

receiving, at a detector at least partially embedded in the eyewear temple of the computerized eyewear, the reflected first signal from the surface of the temple of the wearer over a period of time representative of a movement of the heart rate detection area of the surface of the temple of the wearer;

determining, using a processor at least partially embedded in the eyewear temple, a raw heart rate delta from the reflected first signal;

transmitting, from a second optical transmitter at least partially embedded in the eyewear temple of the computerized eyewear, a second signal to a wide field of detection on the surface of the temple of the wearer that is larger than the heart rate detection area to create a reflected second signal from the surface;

receiving, at the detector of the computerized eyewear, the reflected second signal from the surface of the temple of the wearer over the period of time representative of a movement of the wide field of detection on the surface of the temple of the wearer;

determining, using the processor, a noise delta from the reflected second signal; and determining, using the processor, a measured heart rate of the wearer of the computerized eyewear using the raw heart rate delta and the noise delta.

14. The computer-implemented method of claim 13,
wherein receiving the first signal from the first optical transmitter comprises receiving the first signal emitted from a narrow field emitting LED and reflected back to a detector of the computerized eyewear from a surface of a temple of the wearer, wherein the narrow field emitting LED is operative to focus the first signal on the heart rate detection area of the temple of the wearer, the heart rate detection area comprising a superficial temporal artery of the wearer, and
wherein receiving the second signal from the second optical transmitter comprises receiving the second signal emitted from a wide field emitting LED and reflected back to the detector of the computerized eyewear from the surface of the temple of the wearer, wherein the wide field emitting LED is operative to focus the second signal on the wide field of detection that is larger than the heart rate detection area of the first signal.

15. Computerized eyewear, comprising:
a frame;
an eyewear temple pivotally coupled to the frame, the eyewear temple comprising:
a first optical transmitter at least partially embedded in the eyewear temple and operative to transmit a first signal to a temple of the wearer of the computerized eyewear to measure a raw heart rate delta, and
a second optical transmitter at least partially embedded in the eyewear temple proximate to the first optical transmitter and operative to transmit a second signal to the temple of the wearer of the computerized eyewear to measure a noise delta;
a detector at least partially embedded in the eyewear temple proximate to the first optical transmitter and to the second optical transmitter, the detector operative to receive a reflected first signal originating from the first optical transmitter or a reflected second signal originating from the second optical transmitter and reflected back to the detector from a surface of the temple of the wearer;
at least one processor communicatively coupled to the first optical transmitter, the second optical transmitter, and the detector, the at least one processor operative to use the reflected first signal over time representative of a movement of a heart rate detection area of the surface of the temple of the wearer to generate the raw heart rate delta, to use the reflected second signal over time representative of a movement of a wide field of detection on the surface of the temple of the wearer that is larger than the heart rate detection area to generate the noise delta, and to use the raw heart rate delta and the noise delta to determine a measured heart rate of the wearer of the computerized eyewear.

16. The computerized eyewear of claim 15, wherein the first optical transmitter comprises a narrow field emitting LED operative to focus the first signal on the heart rate detection area of the temple of the wearer, the heart rate detection area comprising a superficial temporal artery of the wearer, wherein the second optical transmitter comprises a wide field emitting LED operative to focus the second signal on the wide field of detection that is larger than the heart rate detection area of the first signal.

17. The computerized eyewear of claim 16, wherein the narrow field emitting LED and the wide field emitting LED are positioned approximately equidistant from and on opposite sides of the detector, and wherein the detector comprises a heart-shaped aperture shaped to enhance detection or differentiation of the reflected first signal and the reflected second signal.

18. The computerized eyewear of claim 15, wherein the first optical transmitter comprises a narrow field emitting LED and the second optical transmitter comprises a wide field emitting LED, and wherein the processor is operative to
measure the time-delay of the light from each LED to the temple of the wearer and back to the photodiode,
utilize the time-delay measurement to determine a first distance between the first optical transmitter and the temple and a second distance between the second optical transmitter and the temple,
repeat the determination of the first distance over a period of time to determine the raw heart rate delta,
repeat the determination of the second distance over the period of time to determine the noise delta, and
isolate a heart rate from the raw heart rate delta and the noise delta to determine the measured heart rate of the wearer.

* * * * *